US012784904B2

(12) United States Patent

Montgomery et al.

(10) Patent No.: US 12,784,904 B2
(45) Date of Patent: Nov. 3, 2026

(54) SYSTEMS AND METHODS FOR LOCALIZED MONITORING OF PATIENTS

(71) Applicant: COVIDIEN LP, Mansfield, MA (US)

(72) Inventors: Dean Montgomery, Edinburgh (GB); Paul S. Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/902,361

(22) Filed: Sep. 30, 2024

(65) Prior Publication Data

US 2025/0246292 A1 Jul. 31, 2025

Related U.S. Application Data

(60) Provisional application No. 63/625,062, filed on Jan. 25, 2024.

(51) Int. Cl.

| | |
|---|---|
| ***G16H 40/20*** | (2018.01) |
| ***G06T 7/00*** | (2017.01) |
| ***G06V 20/52*** | (2022.01) |
| ***G06V 40/10*** | (2022.01) |
| ***G06V 40/20*** | (2022.01) |

(52) U.S. Cl.

CPC ........... *G16H 40/20* (2018.01); *G06T 7/0016* (2013.01); *G06V 20/52* (2022.01); *G06V 40/10* (2022.01); *G06V 40/20* (2022.01); *G06T 2207/30196* (2013.01); *G06T 2207/30232* (2013.01)

(58) Field of Classification Search

CPC .................. G16H 40/20; G06T 7/0016; G06T 2207/30196; G06T 2207/30232; G06V 20/52; G06V 40/10; G06V 40/20

See application file for complete search history.

(56) References Cited

U.S. PATENT DOCUMENTS

| | | | |
|---|---|---|---|
| 10,685,093 | B2 | 6/2020 | McBrearty et al. |
| 11,024,064 | B2 | 6/2021 | Muhsin et al. |

(Continued)

OTHER PUBLICATIONS

H. Liu, Y. Wang and L. Wang, "A review of non-contact, low-cost physiological information measurement based on photoplethysmographic imaging," 2012 Annual International Conference of the IEEE Engineering in Medicine and Biology Society, San Diego, CA, USA, 2012, pp. 2088-2091,doi: 10.1109/EMBC.2012.63 (Year: 2012).*

(Continued)

*Primary Examiner* — Sun M Li

(74) *Attorney, Agent, or Firm* — Dymera IP, LLC

(57) ABSTRACT

A patient monitoring system may include a camera acquiring image data of an environment, a wearable device coupled to a patient and generating sensor data of physiological parameters of the patient, and a computing system communicatively coupled to the camera and the wearable device. The computing system may receive the image data from the camera, receive sensor data indicative of a physiological parameter of a patient, and identify the patient in the image data. The computing system may also associate the physiological parameter with the identified patient in the image data and generate a graphical user interface (GUI) displaying the image data with the physiological parameter overlaid on the displayed image data, where a location of the overlaid physiological parameter on the image data is based on a location of the identified patient in the image data.

20 Claims, 6 Drawing Sheets

(56) References Cited

U.S. PATENT DOCUMENTS

| | | | | |
|---|---|---|---|---|
| 2012/0141000 | A1* | 6/2012 | Jeanne | G06T 7/0016 382/128 |
| 2014/0132413 | A1* | 5/2014 | Fox | A61B 5/02055 340/573.1 |
| 2017/0076042 | A1* | 3/2017 | Katz | G06T 7/70 |
| 2017/0109490 | A1* | 4/2017 | St. Pierre | G06Q 10/00 |
| 2019/0090820 | A1* | 3/2019 | Schwenk | A61B 5/721 |
| 2019/0282324 | A1 | 9/2019 | Freeman et al. | |
| 2021/0212576 | A1* | 7/2021 | MacNeish | A61B 5/0816 |
| 2021/0343017 | A1* | 11/2021 | Jordan | A61B 5/0077 |
| 2022/0167880 | A1* | 6/2022 | Addison | A61B 5/1114 |
| 2022/0326841 | A1 | 10/2022 | Davis et al. | |
| 2023/0084106 | A1 | 3/2023 | Sobol et al. | |
| 2023/0157545 | A1* | 5/2023 | KoKovidis | G16H 20/17 600/301 |
| 2023/0196567 | A1* | 6/2023 | Aykut | G06N 3/0455 382/128 |
| 2023/0200679 | A1* | 6/2023 | Addison | A61B 5/742 600/538 |
| 2023/0397843 | A1* | 12/2023 | Addison | A61B 5/0816 |
| 2025/0107714 | A1* | 4/2025 | Lane | A61B 5/0059 |

OTHER PUBLICATIONS

A. K M, A. Joshy, A. T. George and G. Gopika, "Internet of Healthcare Things (IoHT) Enabled Incessant Real Time Patient Monitoring System Using Non-Invasive Sensors," 2022 10th International Conference on Reliability, Infocom Technologies and Optimization (Trends and Future Directions) (ICRITO),Noida, (Year: 2022).*

Wang et al., "Augmented Reality Navigation With Automatic Marker-Free Image Registration Using 3-D Image Overlay for Dental Surgery," in IEEE Transactions on Biomedical Engineering, vol. 61, No. 4, pp. 1295-1304, Apr. 2014, doi: 10.1109/TBME.2014.2301191 (Year: 2014).*

O. Burgert et al., "Real Time Issues for usage of Vision and Image Data in the Future Operating Room," 2006 IEEE International Conference on Multisensor Fusion and Integration for Intelligent Systems, Heidelberg, Germany, 2006, pp. 285-290, doi: 10.1109/MFI.2006.265665. (Year: 2006).*

T. R. Aditya, S. S. Pai, K. Bhat U, P. Manjunath and G. Jagadamba, "Real Time Patient Activity Monitoring and Alert System," 2020 International Conference on Electronics and Sustainable Communication Systems (ICESC), Coimbatore, India, 2020, pp. 708-712, doi: 10.1109/ICESC48915.2020.9155602. (Year: 2020).*

Hunter, Christophe, et al., Cardiolens: Remote Physiological Monitoring in a Mixed Reality Environment, HAL archives-ouvertes, Sep. 30, 2017, pp. 1-3, https://hal-enac.archives-ouvertes.fr/hal-01598860.

Watch the heart do its job with Cardiolens, Healthiar, Mar. 19, 2018, pp. 1-3, https://healthiar.com/watch-the-heart-do-its-job-with-cardiolens.

* cited by examiner

SYSTEMS AND METHODS FOR LOCALIZED MONITORING OF PATIENTS

CROSS-REFERENCE TO RELATED APPLICATION

This application claims priority to and the benefit of provisional U.S. Patent Application No. 63/625,062, filed Jan. 25, 2024, entitled "SYSTEMS AND METHODS FOR LOCALIZED MONITORING OF PATIENTS," which is hereby incorporated by reference herein in its entirety for all purposes.

TECHNICAL FIELD

The present disclosure generally relates to identifying and associating individual patients in a localized environment with measured physiological parameters.

BACKGROUND

Patients may be monitored in a localized environment (e.g., waiting room, ward, triage) to ensure the well-being and efficient management of patients awaiting medical care. Generally, patients may check-in at a reception desk and provide their personal information as well as a reason for visiting. A clinician (e.g., nurse, doctor, staff) may retrieve electronic health records (EHR) with a medical history of the patient to facilitate the medical care. While the clinician retries the electronic health records, the patient may wait in the localized environment. In certain emergency or urgent care settings, the clinician may perform triage to assess the severity of the patient's condition and prioritize care accordingly.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a patient monitoring system may include a camera that acquires image data of an environment, a wearable device coupled to a patient and generates sensor data of physiological parameters of the patient, and a computing system communicatively coupled to the camera and the wearable device. The computing system may receive the image data from the camera, receive sensor data indicative of a physiological parameter of a patient, and identify the patient in the image data. The computing system may also associate the physiological parameter with the identified patient in the image data and generate a graphical user interface (GUI) displaying the image data with the physiological parameter overlaid on the displayed image data, where a location of the overlaid physiological parameter on the image data is based on a location of the identified patient in the image data.

In another embodiment, a patient monitoring system may include a camera generating image data of an environment, a plurality of wearable devices coupled to a patient and generating sensor data of respective physiological parameters of the patient, and a computing system communicatively coupled to the camera and the plurality of wearable devices. The computing system may receive the image data, receive patient biometric data and association of the plurality of wearable devices with the patient biometric data, and identify the patient in the image data based on the patient biometric data. The computing system may also associate the respective physiological parameters determined from sensor data of the plurality of wearable devices with the identified patient in the image data and generate a graphical user interface (GUI) displaying the image data with the physiological parameters overlaid on the displayed image data based on the identified patient.

In another embodiment, a method of patient monitoring may include, via a processor, receiving image data from a camera within a patient monitoring area and identifying a patient within the image data based on a unique identifier of a wearable device attached to a patient or biometric data of the patient. The method of patient monitoring may also include receiving, via the processor, sensor data indicative of a physiological parameter of the patient from the wearable device and instructing, via the processor, a display device to display a graphical user interface (GUI) comprising the physiological parameter overlaid on the image data.

Various refinements and features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and context of embodiments of the present disclosure without limitation to the claimed subject matter.

BRIEF DESCRIPTION OF THE DRAWINGS

Advantages of the disclosed techniques may become apparent upon reading the following detailed description and upon reference to the drawings in which.

DETAILED DESCRIPTION

Figure 1:
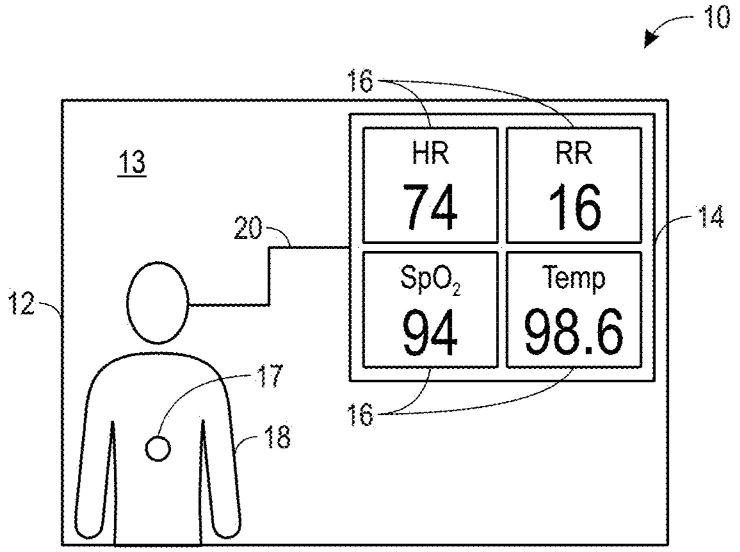
FIG. 1 is a schematic view of an embodiment of a graphical user interface of a patient monitoring system, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

The present disclosure generally relates to the field of patient monitoring, and more particularly, to monitoring one or more physiological parameters of a patient using a patient monitoring system disclosed herein. In embodiments, the disclosed techniques permit visualization of physiological parameter data that is overlaid on a real-time image of a patient or patients in an augmented reality display. In this manner, the caregiver can quickly associate relevant data with the patient or patients. During a check-in process, for example, one or more wearable devices may be attached to the patient to monitor different physiological parameters. As the patient waits in a patient monitoring area (e.g., a localized environment), the wearable devices may monitor the physiological parameters of the patient and generate physiological parameter data. In addition, the patient monitoring area may include one or more cameras that generate image data of the patient monitoring area, such as of the patient and/or the wearable devices. A clinician may view the image data and the physiological parameter information on a display device either within the patient monitoring area or outside of the patient monitoring area, such as at a remote workstation. That is, the clinician may view the patient and their physiological parameters in real-time or near real-time. Thus, the present techniques modify real-time image data of a patient or patients by incorporating associated physiological parameter data to generate an augmented image.

Present embodiments are directed to a patient monitoring system capable of identifying and tracking patients in a localized environment and associating the patients with their respective physiological parameters determined from an attached wearable device. For example, a handshake process may be performed to associate the patient with the one or more attached wearable devices via a unique identifier of the wearable devices. The clinician may input (e.g., scan, manually input) the unique identifier and associate the unique identifier with the patient. In certain instances, the patient monitoring system may track the wearable devices to determine the location of the patient within the patient monitoring area. For example, the patient monitoring system may use triangulation, an object tracking model, Bluetooth, Wi-Fi, radar systems, and the like to determine the location of the wearable devices, and moreover, determine the location of the patient. The patient monitoring system may include a display device that displays image data from one or more cameras and physiological parameters, determined using sensor data, from the one or more wearable devices. As such, the clinician may quickly and efficiently view the patient and their physiological parameters within the patient monitoring area. Additionally or alternatively, the clinician may select the patient or provide other input to the display device indicative of viewing additional information about the patient. In response to the user input, the display device may display a patient history, a patient record, patient information (e.g., name, date of birth, reason for visiting), additional sensor data (e.g., for monitoring physiological parameters over the last 5 minutes, 10 minutes, 15 minutes, 30 minutes), and the like. In this way, the clinician may gain a better understanding of the patient prior to providing medical care.

In certain instances, the patient monitoring system may compare a physiological parameter determined from the image data to a physiological parameter determined from the sensor data to determine a confidence level of the sensor data. For example, the patient monitoring system may determine a respiratory rate from the image data and a respiratory rate from the sensor data. If the value of the respiratory rate from the image data matches the value of the respiratory rate of the sensor data, then the patient monitoring system may maintain or increase a confidence level associated with the sensor data. If the value of the respiratory rate from the image data does not match the value of the respiratory rate of the sensor data, then the patient monitoring system may decrease the confidence level. Additionally or alternatively, the patient monitoring system may hold a previous value of the respiratory rate, which may be associated with a higher confidence level. In other instances, the patient monitoring system may compare a patient motion within the image data to a patient motion within the sensor data. For example, the image data may indicate that the patient may be moving around the patient monitoring area. The patient monitoring system may determine if a heart rate and/or a respiratory rate may be increased due to the movement. If the patient motion in the image data does not match the patient motion within the sensor data, then the patient monitoring system may instruct the display device to output a notification of the discrepancy and/or an indication of unreliable data. As such, the patient monitoring system may improve patient tracking and/or patient monitoring.

Turning now to FIG. 1, an example graphical user interface (GUI) 13 of a display device 12 of the patient monitoring system 10 is illustrated. The patient monitoring system 10 may include or be coupled to the display device 12 that may be located within a patient monitoring area or outside of the patient monitoring area. The display device 12 may include or be implemented on a tablet, a computer, a laptop, a mobile device, a smart phone, and the like. The display device 12 may be used by a clinician (e.g., doctor, nurse, healthcare worker) to view a parameter set 14 including one or more physiological parameters 16 of the patient. The patient monitoring area may be a localized environment (e.g., waiting room, triage). The clinician may, for example, take the display device 12 into the patient monitoring area and view the parameter set 14 associated with the patient or may view the parameter set 14 from a remote workstation.

In another example, the display device 12 may include a headset, smart glasses, a head-mounted display (HMD), and the like. The clinician may walk into the patient monitoring area with the display device 12 and view the parameter set 14 adjacent to the patient, as viewed through the lenses of the display device 12.

As illustrated, the display device 12 may display, on the GUI 13, an acquired image of an environment that includes a visual representation 18 of the patient and a patient-associated parameter set 14 overlaid on the acquired image. In an embodiment, the parameter set 14 is associated with the visual representation 18 via a graphically-generated connecting line or line segments 20 that extend from the overlaid parameter set to the representation 18. However, other graphical association types are also contemplated. For example, the parameter set 14 may be positioned within a certain distance from the visual representation 18. In an embodiment, the parameter set 14 may be positioned at a default location relative to the patient (e.g., above, below, left, right). In an embodiment, the parameter set 14 may be color-coded a same color that is overlaid or otherwise provided on the visual representation 18. In an embodiment, the parameter set 14 may be positioned at a default location relative to the patient (e.g., above, below, left, right). In an embodiment, the overlay of the parameter set 14 may be subject to a rules-based logic that has permitted and excluded overlay conditions. In one example, an overlaid parameter set 14 may not obscure the patient's face and/or another person's face in the acquired image. In an example, the parameter set 14 may be overlaid over a torso of the visual representation 18. Thus, the patient monitoring system 10 may be programmed to identify objects in the image data, such as people (e.g., faces, limbs, torso).

As the patient moves within the localized environment, the overlaid parameter set 14 tracks with or is anchored to updated patient position within the image data. For example, the overlaid parameter set 14 may be positioned proximate to the patient position within the image data. The position of the overlaid parameter set 14 may dynamically change (e.g., adjust) based on the patient position within the image data. For example, when the patient stands up to go to a reception desk, the parameter set 14 moves as the visual representation 18 changes position within the acquired image.

In an embodiment, the visual representation 18 refers to the portion of the image or image data of the localized environment that includes the patient. In embodiments, the visual representation 18 may be a graphical and/or modified representation of the patient image, such as the patient with a blurred face, an overlaid avatar, a stick figure, a cartoon figure, and the like overlaid on the patient image or replacing the patient image. Where available, the visual representation 18 may include patient identifying information. In certain embodiments, the GUI 13 presents the acquired image of the camera, and the visual representation 18 corresponds to a real-time location of the patient within the field of view of the camera. If there are multiple people in the localized environment, the patient monitoring system 10 may identify the patient from the group of people to overlay the parameter set 14 at a location that corresponds to the visual representation 18.

The parameter set 14 may include physiological parameters 16 monitored by one or more wearable devices 17 coupled to (e.g., worn, attached) the patient. The wearable device may include a patch, a band, a wrist-worn device (e.g., watch), a clip-on device, and so on. The patient may wear one or more wearable devices that individually or collectively monitor the physiological parameters 16 within the parameter set 14. By way of example, the physiological parameters 16 may include heart rate, respiration rate, blood oxygen level, and temperature. The physiological parameters 16 may also include motion, position or orientation, blood pressure, glucose level, detection of apnea, patient presence, posture, activity, motion, and so on. Certain contextual parameters, such as patient presence, posture, activity, motion, and so on, may be determined from a combination of sensor data from the wearable device and image data received from one or more cameras within the patient monitoring area. Physiological parameters 16 may include derived values (e.g., trends, variability), combined values, or indexes.

It may be understood that although the illustrated example includes four physiological parameters within the parameter set, any suitable number of physiological parameters may be included in the parameter set. For example, the parameter set may include 1 or more physiological parameters, 2 or more physiological parameters, 3 or more physiological parameters, 5 or more physiological parameters, 6 or more physiological parameters, 7 or more physiological parameters, 8 or more physiological parameters, and so on. Further, it should be understood that the overlaid parameter set 14 may update and change responsive to changing physiological conditions and/or user input. For example, the clinician may select which physiological parameters 16 are displayed on the display device 12. The clinician may want to view blood pressure instead of blood oxygen level or motion instead of temperature. To this end, the display device 12 and/or the GUI 13 may include one or more keys, icons, or buttons that may be used by the clinician to select and/or change the physiological parameters 16. Additionally or alternatively, the clinician may select, on the GUI 13, the visual representation 18 of the patient to receive additional information about the patient, such as a reason the patient may be visiting, the patient's electronic medical records (EMR), information derived from the patient's EMR, pre-existing conditions of the patient, date of last admission, the patient's name, the patient's date of birth, the patient's height, the patient's weight, and so on. The clinician may also select a physiological parameter 16 to view additional sensor data, such trends of the physiological parameter 16 (e.g., values from the past 5 minutes, 10 minutes, 15 minutes, 30 minutes, etc.). In this way, the clinician may efficiently view patient information, such as physiological parameters and/or patient information, about a patient waiting for medical care.

Figure 2:
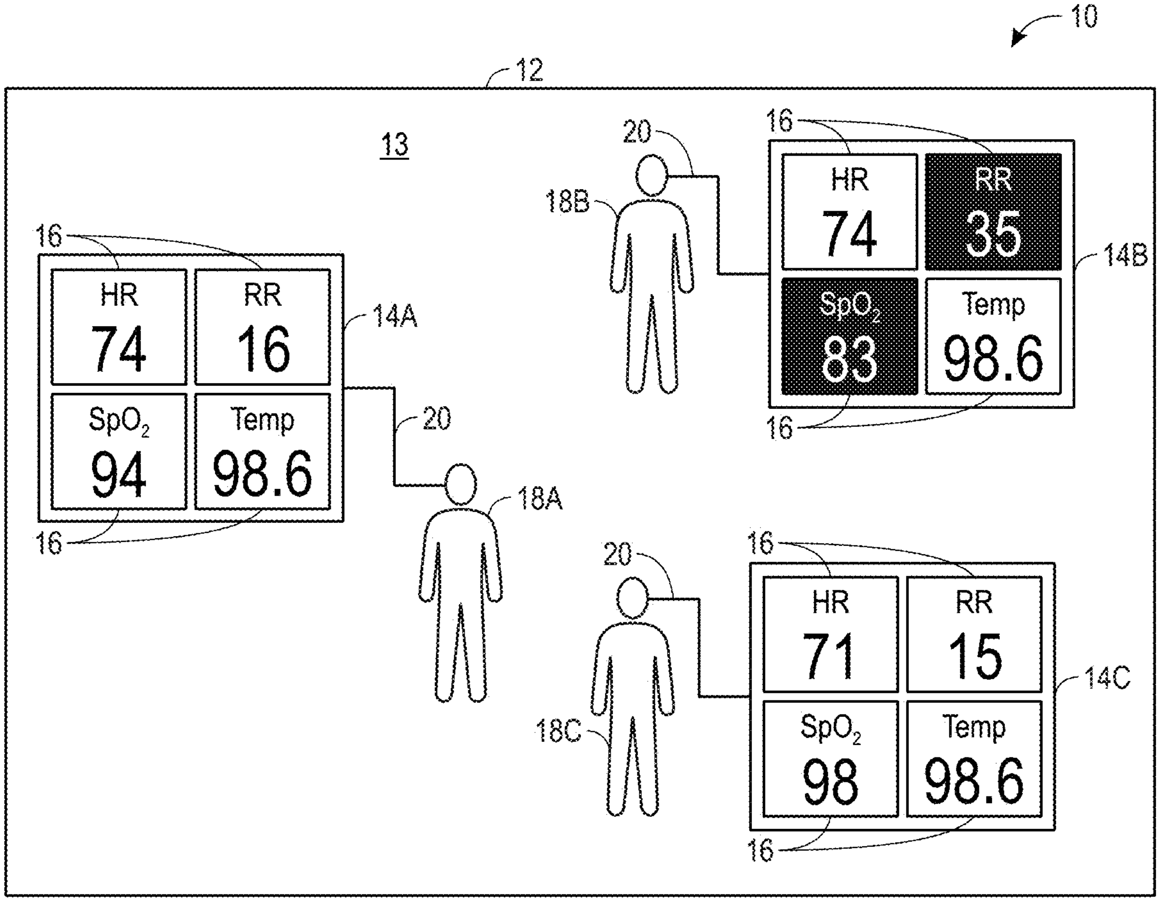
FIG. 2 is a schematic view of an embodiment of a graphical user interface of the patient monitoring system of FIG. 1 monitoring multiple patients and a clinician, in accordance with an aspect of the present disclosure.

FIG. 2 is a schematic view of the GUI 13 of the display device 12 for a patient monitoring system 10 monitoring an environment that includes multiple patients and a clinician. The patient monitoring system 10 is capable of distinguishing between different individuals to associate physiological parameters to the appropriate subject. As illustrated, the display device 12 may display, on the GUI 13, a first visual representation 18A of a first patient associated with a first parameter set 14A via connecting lines 20, a second visual representation 18B of a second patient associated with a second parameter set 14B via connecting lines 20, and a third visual representation 18C of a clinician coupled to a third parameter set 14C via connecting lines 20. The patients and/or the clinician may be standing, sitting, laying in bed, walking, and the like within the patient monitoring area.

In the illustrated example, the GUI 13 may include warning or alarm designations in particular parameters sets 14 to permit a rapid assessment of physiological condition for a group of monitored individuals, such as in a triage setting. For example, the parameter set 14B may have one or more alarm conditions in the physiological parameters 16.

The alarm conditions for an individual physiological parameter 16 may be based on pre-determined ranges, thresholds, machine learning outputs, etc. The alarm identification may be performed by the patient monitoring system 10 or may be based on communication from a coupled system that receives the data from the wearable device. In the illustrated example, the parameter set 14B of the second patient may include two physiological parameters 16 outside of respective pre-determined ranges. As illustrated, the respiratory rate may be 35 breaths per minute, which may be greater than the pre-determined range for respiratory rate, and the blood oxygen level may be 83%, which may be lower than the pre-determined range for blood oxygen level. The respiratory rate and the blood oxygen level may be highlighted in a color (e.g., red), to provide a visual indication that the value is outside of a respective pre-determined range (e.g., threshold value, threshold range). In contrast, the heart rate and the temperature, which may be within the respective pre-determined ranges, may be displayed in a second color (e.g., blue) to provide a visual indication that the value is within a respective pre-determined range. In other examples, the physiological parameters 16 outside of a respective pre-determined range may include a flag, an exclamation point, a gradient, or the like to provide a visual indication (e.g., notification) that the value may be outside of the respective pre-determined range. In an embodiment, the GUI 13 may include an animation (e.g., pulsing, expanding) associated with an alarm condition. As such, the clinician may view the display device 12 and quickly identify physiological parameters 16 outside of pre-determined ranges when present for a particular patient.

In certain instances, the patient monitoring system 10 may extend to clinicians to monitor their physiological parameters 16 while working, which may improve working conditions for the clinicians. The physiological parameters 16 of the clinicians being monitored may be the same or different from the physiological parameters 16 of the patients. For example, as illustrated, the physiological parameters 16 of the clinicians being monitored include a heart rate, a respiration rate, a blood oxygen level, a temperature. In another example, the physiological parameters 16 of the clinicians being monitored may include a stress level, a blood pressure level, a walking speed, a temperature, and so on. The parameter set 14C including the physiological parameters 16C of the clinician may be presented a different color (e.g., third color) in comparison to the parameter set 14A, 14B of the patient. Additionally or alternatively, the third visual representation 18C of the clinician may be different from the visual representation 18A, 18B of the patient to provide a distinction between the two groups.

When a patient and/or the clinician leaves the patient monitoring area (e.g., a field of view of the cameras), the patient monitoring system 10 may continue to track the patient and/or the clinician between the different locations and re-display the visual representation 18A, 18B, 18C of the patient and/or the clinician in the new room with the respective parameter set 14A, 14B, 14C. For example, when the patient gets moved into another room or if the clinician visits a different room, the patient and/or the clinician may be recognized in the new room based on biometric data, the image data from the cameras, and/or image analysis techniques. Additionally or alternatively, the patient and/or the clinician may be recognized in the new room based on the wearable device, radar, Bluetooth, Wi-Fi, and so on.

In the illustrated embodiment, the overlay of the parameter sets 14 on the GUI 13 may be positioned relative to the respective visual representations 18 in the image data such that the parameter sets 14 are non-overlapping with one another and such that an individual parameter set 14 is associated with a particular visual representation 18. Thus, a rules-based logic may be used to visually separate different parameter sets 14 to prevent confusion. For example, connecting lines 20 for different parameter sets 14 may be programmed not to intersect one another. A particular parameter set 14 may be required to be a certain distance away from non-associated visual representations 18. In cases where the localized environment is crowded, the patient monitoring system 10 may permit at least partial overlay of the parameter sets 14 onto images of individuals not being monitored (e.g., family members).

Figure 3:
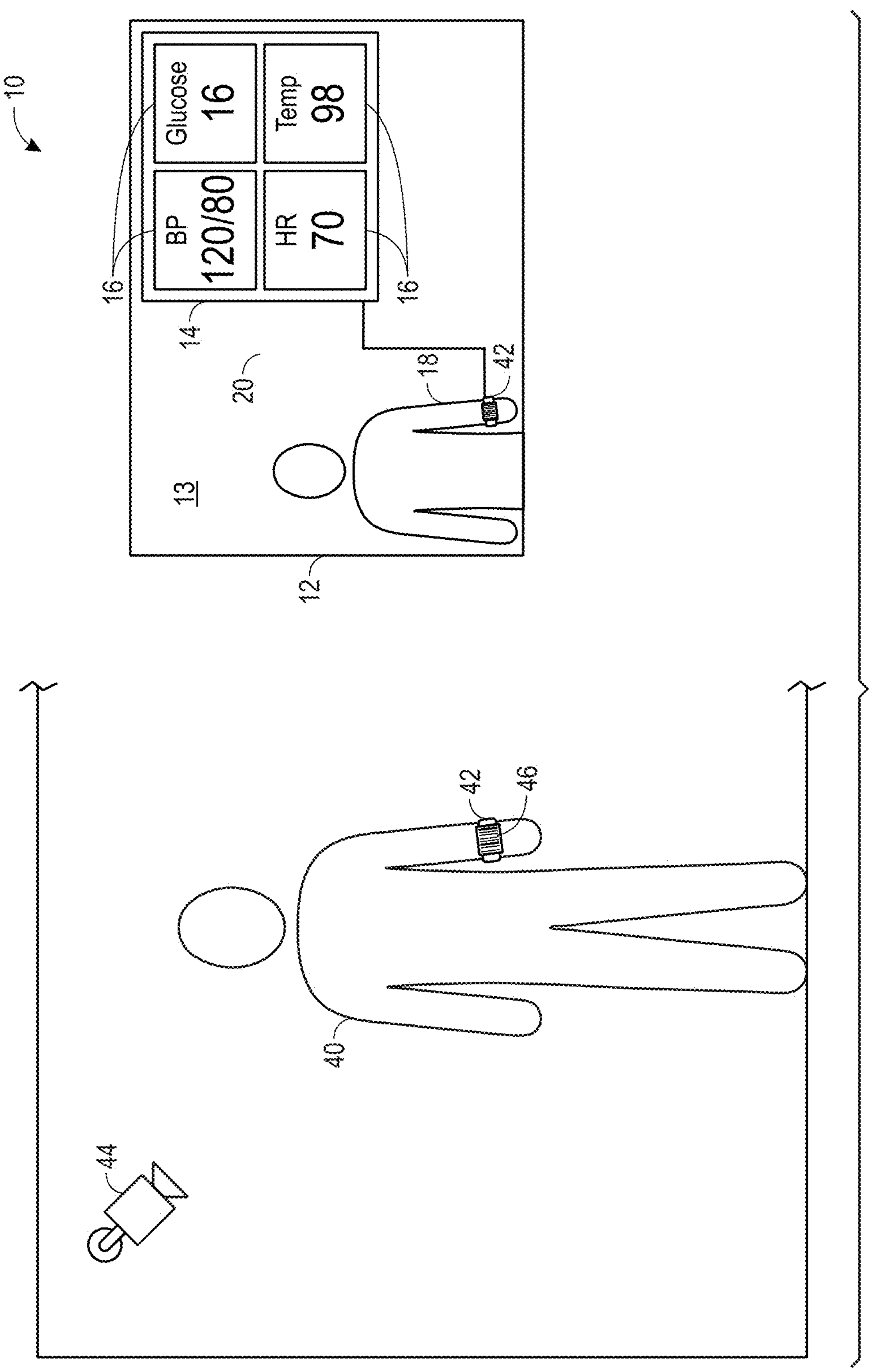
FIG. 3 is a schematic view of an embodiment of the patient monitoring system of FIG. 1 monitoring a patient via a display device, in accordance with an aspect of the present disclosure.

FIG. 3 is a schematic view of the patient monitoring system including a camera 44 that captures image data. In certain cases, the camera 44 may be a fixed camera in the localized environment. Alternatively or additionally, the camera 44 may be an integral camera of a tablet or a smart phone (e.g., a rear camera). For example, a clinician may hold the display device 12 in front of a patient such that the patient 40 appears in a field of view of the camera 44. The image data from the camera 44 may be used to populate the GUI 13 displayed on the display device 12 along with the parameter set 14 with the physiological parameters 16 of the patient 40. In an embodiment, the parameter set 14 may overlaid at a position associated with a visual representation 41 of a wearable device 42 attached to the patient 40. In certain instances, if the patient 40 wears multiple wearable devices 42, each physiological parameter 16 may appear to be coupled to a respective wearable device 42 that monitors and/or generates the physiological parameter 16. For example, a respiration rate may appear to be coupled to a wearable device 42 on a chest area of the visual representation 18 of the patient while a heart rate may appear to be coupled to a wearable device 42 on wrist area of the visual representation 18 of the patient. In this way, the clinician may view the parameter set 14 in real-time or near real-time, which may facilitate improved medical care.

The wearable device 42 may include a patch, a band, a wrist-worn device (e.g., watch), a clip-on device, and so on. The patient 40 may be attached to one or more wearable devices 42 that individually or collectively monitor the physiological parameters 16 of the patient 40. For example, as illustrated, the wearable device 42 may be a wrist-worn device (e.g., watch, blood pressure cuff). The wearable device 42 may include a unique identifier 46, such as a barcode, a QR code, a pattern, a string of numbers, a string of letters, a string of letters and numbers, and so on, that may be used to identify the wearable device 42 and associate the wearable device 42 with the patient 40. For example, the clinician may enter the unique identifier 46 into a computing system to associate the patient 40 with the wearable device 42, and furthermore, to associate the visual representation 18 of the patient 40 with the physiological parameters 16 monitored by the wearable device 42.

In certain instances, the wearable device 42 may be within the field of view of the camera 44 and the patient 40 may be identified based on the wearable device 42. For example, the image data may include a clear view of the unique identifier 46 but an obscured view of the patient 40 due to the patient moving, such as to blow their nose, to talk to another patient, and/or to move around the patient monitoring area. As such, the patient 40 may be identified within the image data based on the unique identifier 46 of the wearable device 42. In another example, the wearable device 42 may communicate via Bluetooth or Wi-Fi within the patient monitoring area. The location of the wearable device 42 within the patient monitoring area may be determined based on signals transmitted over Bluetooth or Wi-Fi and a corresponding location within the image data may be determined. In certain cases, the transmitted data may include information associated with the unique identifier 46 or may be associated with the unique identifier 46, permitting automatic association of transmitted sensor data with the patient 40. The location may be associated with the patient 40. As such, the patient 40 may be identified and tracked based on the unique identifier 46 and/or the wearable device 42.

In other instances, patients 40 may be positioned close to each other, which may result in a crowding issue. If the patients 40 may not be accurately identified within the image data, the patients 40 may be identified based on the attached wearable devices 42. However, if the patients 40 may not be identified based on the attached wearable devices 42, then the GUI may display a warning that the sensor data may be unreliable.

Figure 4:
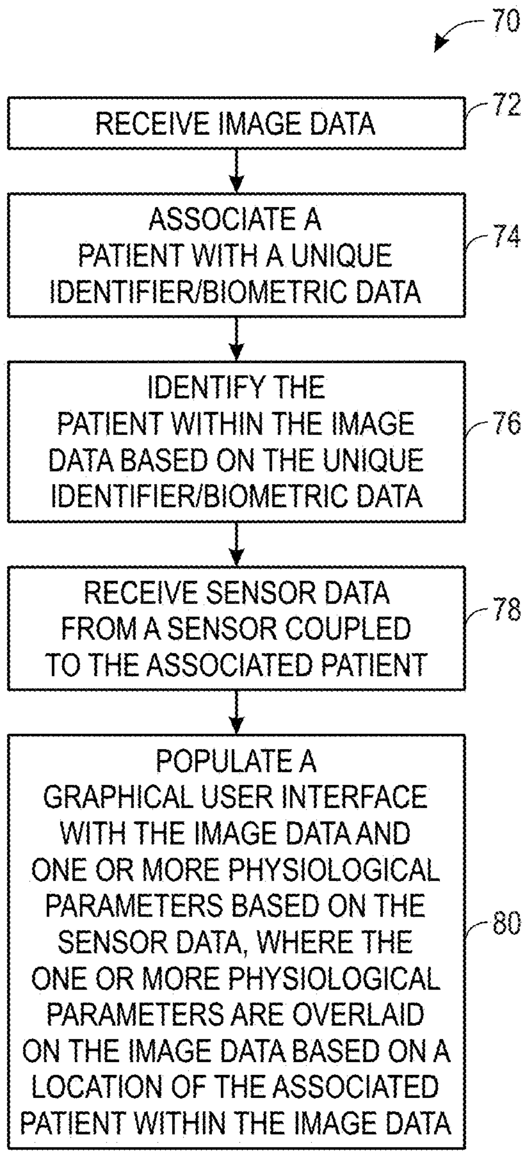
FIG. 4 is a flowchart of an example method for operating the patient monitoring system of FIG. 1 to populate a graphical user interface with physiological parameters overlaid on image data, in accordance with an aspect of the present disclosure.

FIG. 4 is a flowchart of an example method 70 for operating the patient monitoring system to populate the GUI with sensor data and image data. For example, one or more wearable devices may be attached to the patient during a check-in process to monitor one or more physiological parameters of the patient. A handshake process may be performed to associate each of the one or more wearable devices with the patient. For example, each wearable device may include a unique identifier that may be inputted by the clinician to a computing system to associate the wearable device with the patient. In addition, a photo or a video of the patient may be taken. The unique identifier of the wearable device may be associated with the photo or video of the patient to identify and/or track the patient within the patient monitoring area. While the illustrated example of FIG. 4 includes identifying and tracking a patient, the method of FIG. 4 may also be used to identify and track a clinician within the patient monitoring area.

At block 72, image data may be received. For example, one or more camera(s) within the patient monitoring area may generate and transmit image data (e.g., camera data) to a computing system and/or a display device. The image data may include one or more patient(s) within the patient monitoring area and/or wearable devices attached to the patient(s). For example, the patient monitoring area may include multiple cameras positioned at different locations of the patient monitoring area to provide a complete top-down (e.g., bird's eye) view of the area. Image data from each of the cameras may be processed (e.g., stitched together) to provide the complete view.

At block 74, the patient may be associated with the unique identifier or the biometric data. As discussed herein, a handshake process may be initiated to associate the wearable device and the patient during the check-in process. For example, prior to a patient entering the patient monitoring area, a clinician may attach a wearable device to the patient. The clinician may also open a patient profile and/or information regarding the patient. The clinician may scan a unique identifier of the wearable device to associate the wearable device with the patient profile. This may associate the wearable device and/or any sensor data generated by the wearable device with the patient. In addition, the unique identifier of the wearable device may be used to identify and/or track the patient within the patient monitoring system. In certain instances, biometric data of the patient may be generated and added to the patient profile. For example, the clinician may take a photo or a video of the patient and add the biometric data to the patient profile. As such, the patient may be associated with their biometric data and/or the unique identifier of the attached wearable device. In certain instances, one or more wearable devices may be attached to the patient.

At block 76, a patient within the image data may be identified based on a unique identifier or biometric data. For example, the image data may include the patient in the patient monitoring area. The patient may be identified based on the unique identifier of the wearable device attached to the patient. The image data may include the wearable device as well as the unique identifier of the wearable device. The unique identifier within the image data may be processed (e.g., identified, isolated) based on image analysis techniques and/or computer vision techniques. The unique identifier within the image data may be matched to unique identifiers associated with patients to identify the respective patient associated with the processed unique identifier. In another example, the image data may include a profile (e.g., facial features, body features) of the patient. The profile of the patient may be processed using image analysis techniques and/or computer vision techniques. The profile of the patient may be matched to biometric data to identify the respective patient.

At block 78, sensor data from a sensor coupled to the patient may be received. Each of the wearable device attached to the patient may monitor and transmit sensor data to a computing system. In an embodiment, the sensor data may include one or more physiological parameter(s) of the patient. That is, the physiological parameter(s) may be calculated on-board the wearable device or by an intervening device before being transmitted to the computing system. Additionally or alternatively, the computing system may operate on the sensor data to calculate the physiological parameter(s). The wearable device(s) may continuously or intermittently transmit the sensor data while in operation.

At block 80, a graphical user interface (GUI) may be populated with the image data and the physiological parameter(s), where the physiological parameter(s) is overlaid based on a location of the associated patient within the image data. The computing system may receive the sensor data from the wearable device and the image data from the camera(s) and generate a GUI including both the image data and one or more physiological parameters based on or included in the sensor data. The computing system may display the image data and a parameter set including the physiological parameter in a location proximate to the patient within the image data. The parameter set may be coupled to the patient within the image data, a wearable device coupled to the patient within the image data, a visual representation of the patient within the image data, and the like. For example, the parameter set may track with or anchored to the patient within the image data even if the patient moves around the patient monitoring area. In certain instances, the computing system may blur or obscure (e.g., exclude) the patient's face within the image data. In other instances, the computing system may substitute the representation of the patient within the image data with an avatar. Additionally or alternatively, the computing system may provide a visual indication if a value of the physiological parameter is outside of a pre-determined range or otherwise corresponds to an alarm condition for that parameter. As such, a clinician viewing the GUI may quickly identify at-risk patients. In certain instances, the clinician may prioritize an at-risk patient for receiving medical care.

The methods discussed herein include various steps represented by blocks in flow diagrams. It should be noted that at least some steps may be performed as an automated procedure by one or more components of a system. Although the flow diagrams may illustrate the steps in a certain sequence, it should be understood that the steps may be performed in any suitable order and certain steps may be carried out simultaneously, where appropriate. Additionally, steps may be added to or omitted from the methods.

Figure 5:
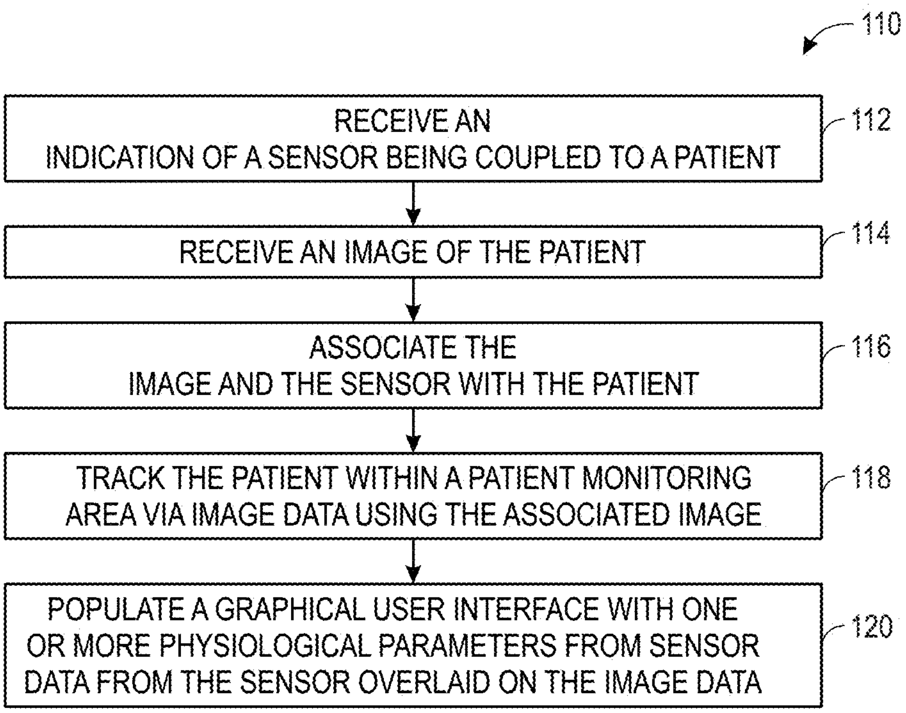
FIG. 5 is a flowchart of an example method for operating the patient monitoring system of FIG. 1 performing a handshake to associate a wearable device with a patient, in accordance with an aspect of the present disclosure.

FIG. 5 is a flowchart of an example method 110 for operating the patient monitoring system performing a handshake process to associate a wearable device with a patient. At block 112, an indication of a sensor being coupled to a patient may be received. For example, a clinician may enter a unique identifier of a wearable device into the computing system and the clinician may then attach the wearable device to the patient. The unique identifier may be typed in, scanned via a bar chart, photographed, or videoed by the clinician to be entered into the computing system. In addition, the clinician may attach multiple wearable devices to the patient, where each wearable device may monitor a different physiological parameter of the patient. For example, a first wearable device may monitor a heart rate, a temperature, and a patient activity, a second wearable device may monitor a respiration rate, and a third wearable device may monitor a blood oxygen level.

At block 114, an image of the patient may be received. For example, the clinician may take a video or a photo of the patient's face and/or body and provide the photo or the video to the computing system. That is, the clinician may generate biometric data of the patient.

At block 116, the patient image and the sensor may be associated with the patient. For example, the unique identifier of the wearable device may be associated with biometric data of the patient. Both the wearable device and the biometric data may be associated with the patient, such as a patient electronic medical record, a patient identifier, a patient name, and the like. If the patient is attached to multiple wearable devices, the computing system may associate the unique identifier of each wearable device with the biometric data and/or the patient.

At block 118, the patient may be tracked within a patient monitoring area via image data using the associated image. The computing system may receive image data with one or more patients from cameras within the patient monitoring system and identify the patient within the image data based on the biometric data. For example, the computing system may determine a match between a visual representation of the patient within the image data and the biometric data to track the patient. Additionally or alternatively, as discussed herein, the patient may be tracked based on the wearable device, e.g., via triangulation of transmitted signals.

At block 120, a graphical user interface may be populated with the image data and one or more physiological parameters from sensor data from the sensor the image data overlaid on the image data, similar to block 80 described with respect to FIG. 4. For example, the computing system may display image data from the camera and overlaid the parameter set and/or a physiological parameter at a location proximate the patient within the image data. The parameter set and/or the physiological parameter may visually appear to be coupled to the patient (e.g., a body part of the patient) or the sensor coupled to the patient within the image data via a connecting line. In another example, the computing system may display the visual representation (e.g., avatar) of the patient within the image data and a parameter set including the physiological parameter from the sensor data on the GUI at a location proximate to the visual representation.

The methods discussed herein include various steps represented by blocks in flow diagrams. It should be noted that at least some steps may be performed as an automated procedure by one or more components of a system. Although the flow diagrams may illustrate the steps in a certain sequence, it should be understood that the steps may be performed in any suitable order and certain steps may be carried out simultaneously, where appropriate. Additionally, steps may be added to or omitted from the methods.

Figure 6:
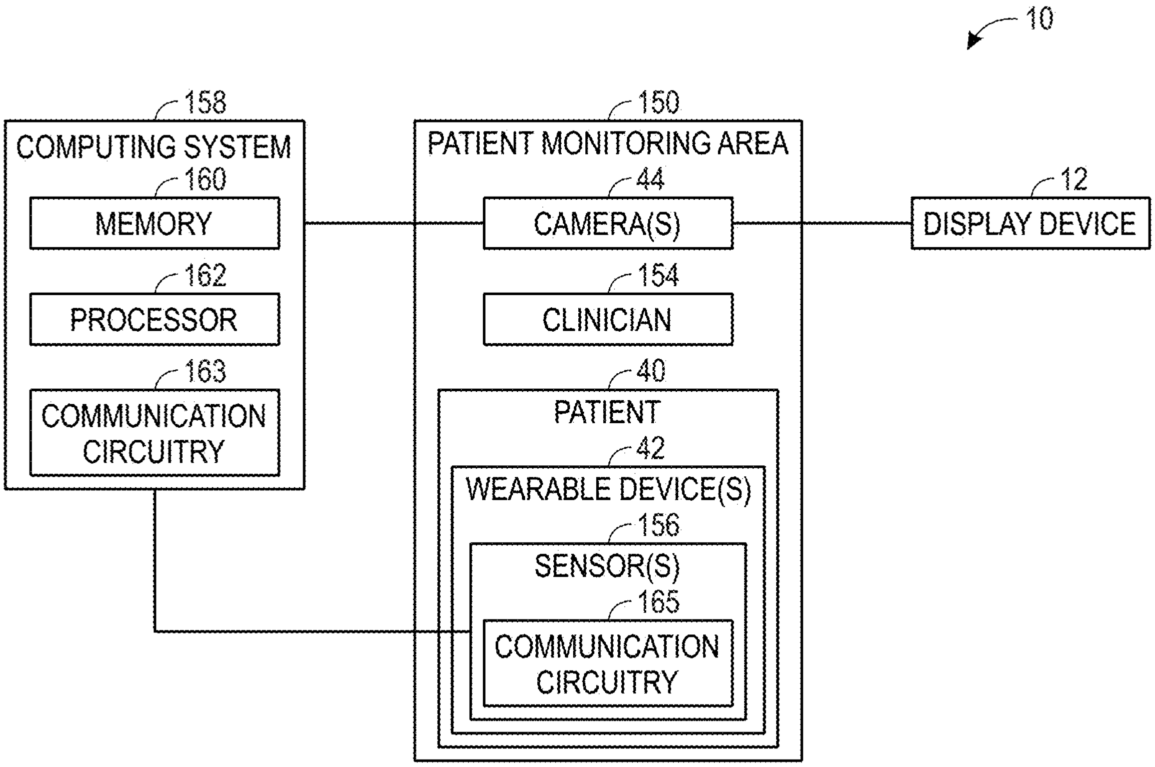
FIG. 6 is a block diagram of the patient monitoring system of FIG. 1, in accordance with an aspect of the present disclosure.

FIG. 6 is an example block diagram of the patient monitoring system 10. The patient monitoring system 10 may be implemented in a patient monitoring area 150 with one or more camera(s) 44, a clinician 154, and a patient 40. The patient monitoring area 150 may be a localized environment, such as a waiting room of an urgent care center, a waiting room of an emergency room, a waiting room of a hospital, a waiting room of a clinic, a ward, a triage, and so on. Although the illustrated example of FIG. 6 includes a patient monitoring area 150, a patient 40, and a clinician 154, the patient monitoring system 10 may include multiple patient monitoring area(s) 150 with one or more patient(s) 40 waiting to receive medical care and/or one or more clinicians 154 facilitating the medical care.

The patient monitoring area 150 may also include one or more camera(s) 44 that generate image data of the patient 40 within the patient monitoring area 150. The camera(s) 44 may include a thermal light camera, a light-based camera (e.g., RBG camera, IR camera), a depth-based camera, a hyperspectral camera, and the like. The patient monitoring area 150 may include multiple cameras 44, which may be different types of cameras, positioned in different locations of the patient monitoring area 150, to provide a complete view. For example, the image data from each camera 44 may be processed (e.g., overlaid, stitched) to form the complete view.

The camera(s) 44 may be a camera communicatively coupled to a display device 12. The display device 12 may display the image data from the camera(s) 44, visual representations of the patient 40, visual representations of the clinician(s) 154, parameter set(s) 14, environmental conditions, and so on. As discussed herein, the display device 12 may include a laptop, a tablet, a computer, a mobile device, and the like. For example, the display device 12 may be a tablet (e.g., a portable device) that the clinician may view the patient 40 within the patient monitoring area 150 and associated parameter sets 14. The clinician 154 may take the display device 15 into and out of the patient monitoring area 150. As discussed with respect to FIGS. 1 and 2, the clinician 154 may view the patient 40 via the display device 12 within the patient monitoring area 150 or outside of the patient monitoring area 150, such as at a remote station or a central station. As discussed with respect to FIG. 3, the clinician 154 may view the patient 40 via the display device 12 by using a camera on the display device 12 to capture image data of the patient 40. In other instances, the display device 12 may include smart glasses, a head set, and so on that may be worn by the clinician 154 to view the image data and the parameter set 14. For example, the clinician 154 may wear smart glasses to view the patient avatar, the parameter set 14, one or more physiological parameters 26, and so on. In another example, the clinician 154 may put on a headset at a remote station to virtually inhabit the patient monitoring area 150 and view the parameter set 14 attached to each patient avatar.

The patient 40 may arrive at the patient monitoring area 150 and go through a check-in process. For example, the clinician 154 may register the patient 40, take vital signs of the patient 40, and/or attach one or more wearable devices 42 to the patient 40. The clinician may scan or input a unique identifier 46 of the wearable device 42 to identify and associate the wearable device 42 with a patient 40 and/or the patient's record. Each wearable device 42 may include one or more sensor(s) 156 that monitor a physiological parameter of the patient 40. For example, the sensor(s) 156 may monitor a temperature level, a blood oxygen level, a blood pressure level, a heart rate, a respiration rate, a patient activity (e.g., motion), and so on. In certain instances, the sensor(s) 156 may also monitor environmental conditions of the patient monitoring area 150, such as a sound level, a temperature level, a light level, a toxicity level, and so on. Additionally or alternatively, the patient monitoring area 150 may include one or more additional sensor(s) that monitor the environmental conditions. For example, the patient monitoring area 150 may include smart devices with a sensor, such as a smart thermostat, smart blinds, and the like.

In addition to providing sensor data, the wearable device 42 may also provide operating information of the wearable device 42. The operating information may include an amount of remaining battery, a signal strength, a connection method (e.g., Wi-Fi, Bluetooth), a connection strength, and the like. In certain instances, the wearable device 42 may provide an alert when the amount of battery (e.g., battery life) is below a threshold (e.g., 10%, 20%) or when the connection strength is weak (e.g., below a threshold). Additionally or alternatively, the wearable device 42 may provide an indication when the connection strength is strong.

To implement the patient monitoring process, the patient monitoring system 10 may include a computing system 158 (e.g., a control system, an automated controller, a programmable controller, an electronic controller, control circuitry, a cloud-computing system) configured to receive data from the camera(s) 44 and the sensor(s) 156 and generate a GUI for display on the display device 12. The computing system 158 may include a memory 160 (representative of one or more memories) and processing circuitry or a processor 162 (representative of one or more processors), and communication circuitry 163 (e.g., transceivers, radio communication circuitry) to communicate with communication circuitry 165 of the sensor(s) 156, e.g., to receive sensor data. The memory 160 may include volatile memory, such as random-access memory (RAM), and/or non-volatile memory, such as read-only memory (ROM), optical drives, hard disc drives, solid-state drives, or any other non-transitory computer-readable medium that includes instructions identify the patient 40 within the image data and/or generate the GUI for display on the display device 12. The memory 160 may also include an object tracking model, a computer vision algorithm, an object tracking algorithm, a deep learning algorithm, and the like. The processor 162 may be configured to execute such instructions. For example, the processor 162 may include one or more application specific integrated circuit(s) (ASICs), one or more field programmable gate array(s) (FPGAs), one or more general-purpose processor(s), or any combination thereof. The computing system 158 may include additional components such as a display, one or more input/output ports, communication ports, a camera, and the like. Although the computing system 158 and the display device 12 are illustrated as individual components, in certain instances, the computing system 158 and the display device 12 may be the same component.

The computing system 158 may associate the wearable device 42 with the patient 40 via a unique identifier 46 of the wearable device 42 and/or biometric data. For example, the clinician 154 may input the unique identifier 46 of the wearable device 42 into the computing system 158. The computing system 158 may identify a type of the wearable device 42, a function of the wearable device 42, an amount of battery remaining within the wearable device 42, and the like in response to receiving the unique identifier 46 of the wearable device 42. The computing system 158 may associate the wearable device 42 with the patient 40 and/or the patient's record. Further, the clinician 154 may also take a video and/or a picture of the patient's face and/or body to generate biometric data and associate the biometric data with the patient 40 and/or the patient's record. The computing system 158 may also associate the unique identifier 46 with the biometric data to track the patient 40 within the patient monitoring area 150. With respect to the patient's records, the computing system 158 may be communicatively coupled to a database or cloud server database storing the patient's records via a network. access the patient's record stored in a database or a cloud server via a network. In certain instances, the patient's records may be stored in the computing system 158.

In other instances, the computing system 158 may track a patient 40 within the patient monitoring area 150 via the wearable device 42. In an instance, the computing system 158 may use triangulation of the wearable device 42 to determine the location of the wearable device 42 within the patient monitoring area 150 and associate the location of the wearable device 42 as the location of the patient 40. In other instances, the computing system 158 receive signals from a millimeter wave radar system, Bluetooth signals, Wi-Fi signals, an object tracking model, and the like to track the wearable device 42. For example, the computing system 158 may use an object tracking model to continuously track the patient from the time the wearable device 42 is coupled to the patient 40. In another example, the computing system 158 may use a computer vision object tracking algorithm, or a deep learning based approach to identify and track the patient within the patient monitoring area 150. The computing system 158 may use any or a combination of these techniques to track the patient 40 in the patient monitoring area 150 and/or other environments, such as if the patient 40 moves from one room to another room.

The computing system 158 may populate the GUI (e.g., GUI 13) with the sensor data and the image data for display on the display device 12. As discussed with respect to FIGS. 1-3, the computing system 158 may populate the GUI with a visual representation 18 of the patient 40, a parameter set 14 including one or more physiological parameters 16, a connecting line 20, a visual representation 41 of a wearable device 42, and the like. The computing system 158 may use the sensor data from one or more wearable device(s) 42 to generate the parameter set 14 and the image data from the one or more camera(s) 44 to generate a view of the patient monitoring area 150. In certain instances, the computing system 158 may generate the an avatar corresponding to the patient 40 populate the GUI. The computing system 158 may continuously update the GUI in real-time or near real-time.

In certain instances, the computing system 158 may identify periods of unreliable data and output a notification. As will be discussed with respect to FIG. 7, the computing system 158 may identify patient activity within the image data over a period of time and determine if there may be patient activity within the sensor data over the period of time. If the patient activity between the image data and the sensor data does not match, then the computing system 158 may output a notification to alert the clinician 154 to potentially unreliable data. For example, the notification may alert the clinician 154 that the wearable device 42 may be detached from the patient 40, out of battery, not functioning properly, and so on. As will be discussed with respect to FIG. 8, the computing system 158 may identify a physiological parameter 16 of a patient 40 within the image data over a period of time and determine if a value of the physiological parameter 16 from the image data matches a value of a physiological parameter from the sensor data. As such, patient monitoring may be improved.

Figure 7:
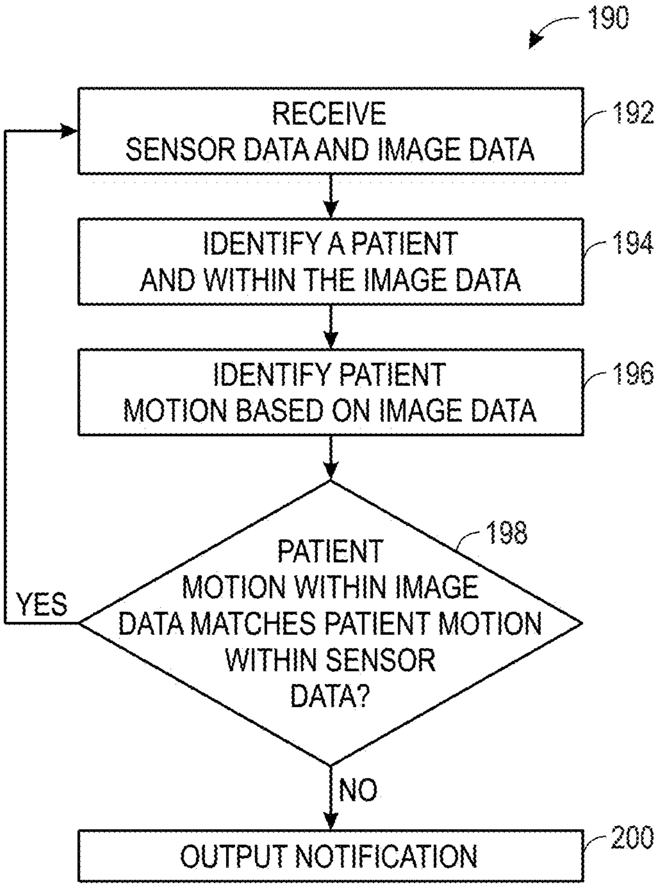
FIG. 7 is a flowchart of an example method for operating the patient monitoring system of FIG. 1 to identify an unreliable sensor based on image data and sensor data, in accordance with an aspect of the present disclosure.

FIG. 7 is a flowchart of an example method 190 for operating the patient monitoring system to identify an unreliable sensor based on image data and sensor data. For example, a physiological parameter may be determined by both sensor data and image data to improve reliability and/or operation of the patient monitoring system. For example, an accelerometer of the wearable device may indicate that the patient may be moving and the sensor data may include that a heart rate may be increasing. The computing system may determine that the accelerometer data and the sensor data may match and increase a confidence level. If the accelerometer data indicates that the patient may be moving but the sensor data indicates that the heart rate is steady or decreasing, then the computing system may determine that the accelerometer data and the sensor data may not match and output a notification of the discrepancy. For example, the computing system may lower a quality flag (e.g., confidence level, reliability level).

At block 192, sensor data and image data may be received. For example, the computing system may receive sensor data from the wearable devices attached to the patient and the image data from the cameras within the patient monitoring area.

At block 194, a patient within the image data may be identified, similar to block 74 discussed with respect to FIG. 4. For example, the computing system may identify the patient within the image data based on the unique identifier of the wearable device and/or biometric data of the patient.

At block 196, patient motion may be identified based on the image data. The computing system may use image analysis techniques and/or computer vision techniques to identify movement (e.g., activity) of the patient within the image data. For example, the patient may be walking within the patient monitoring area and the computing system may identify the walking motion. In another example, the patient may be fidgeting in a chair and the computing system may identify the fidgeting. Still in another example, the patient may be sitting or standing without moving, and the computing system may identify the patient activity as not moving. Additionally or alternatively, the computing system may identify one or more physiological parameters based on the camera data. For example, the computing system may identify a respiratory rate, a patient presence, a posture, and the like.

At determination block 198, patient motion within image data matching patient motion within sensor data may be determined. The computing system may determine if the patient movement (e.g., activity) within the camera data matches a number of motion artifacts within the sensor data. For example, the patient may be moving across the patient monitoring area, which may introduce motion artifacts into the sensor data. In another example, the patient may be sitting or standing without motion, which may result in the sensor data being generated without or with insignificant amounts of motion artifacts.

If the patient motion within the image data matches the patient motion within the sensor data, then the method 190 may return to block 192 to receive sensor data and image data. For example, if the image data indicates that the patient is moving and the sensor data also includes motion artifacts, then the computing system may determine a match. In certain instances, the computing system may hold a previous value or mark a corresponding time period as unreliable data. For example, the computing system may lower a quality flag and provide an indication on the GUI to alert the clinician to the potentially unreliable data. In another example, if the image data indicates that the patient is not moving and the sensor data also does not include motion artifacts, then the computing system may determine a match. The computing system may raise or maintain a quality flag and provide an indication on the GUI of the reliable data.

If the patient motion within the image data does not match the patient motion within the sensor data, then at block 200, a notification may be outputted. For example, the image data may indicate that the patient may be moving across the patient monitoring area, but the sensor data may not include any motion artifacts. In another example, the image data may indicate that the patient may not be moving, such as sitting or standing, while the sensor data includes motion artifacts. The computing system may populate the graphical user interface with a notification indicating the discrepancy. For example, the notification may alert the clinician to check on the wearable device attached to the patient. In certain instances, the wearable device may fall off the patient, become detached from the patient, be transmitting data unreliably, stop functioning, and the like. The clinician may restart the wearable device, reattach the wearable device to the patient, and the like. As such, unreliable data may not be displayed on the graphical user interface and patient monitoring may be improved.

The methods discussed herein include various steps represented by blocks in flow diagrams. It should be noted that at least some steps may be performed as an automated procedure by one or more components of a system. Although the flow diagrams may illustrate the steps in a certain sequence, it should be understood that the steps may be performed in any suitable order and certain steps may be carried out simultaneously, where appropriate. Additionally, steps may be added to or omitted from the methods.

Figure 8:
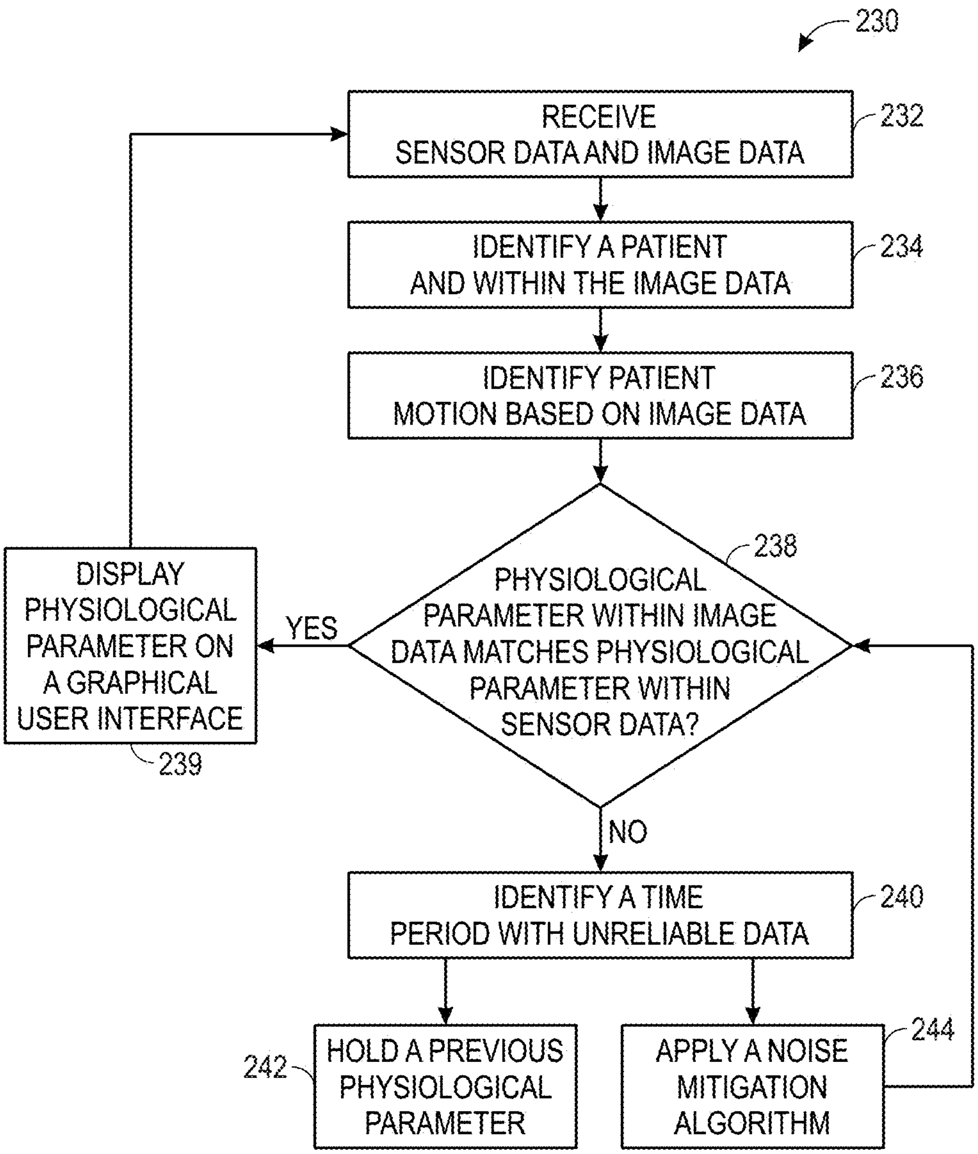
FIG. 8 is a flowchart of an example method for operating the patient monitoring system of FIG. 1 to identify unreliable sensor data over a period of time, in accordance with an aspect of the present disclosure.

FIG. 8 is flowchart of an example method 230 for operating the patient monitoring system to identify unreliable sensor data over a period of time. For example, the image data may show the patient moving, which may provide an indication that the sensor data may include motion artifacts. As such, the physiological parameters measured by the wearable device may be unreliable (e.g., inaccurate), and the computing system may instruct the display to hold and display a last physiological parameter on the GUI. In addition, the patient monitoring system may mark the period of time as unreliable data, which may improve patient monitoring.

At block 232, sensor data and image data may be received, similar to block 192 described with respect to FIG. 7. At block 234, a patient within the image data may be identified, similar to block 74 described with respect to FIG. 4 and block 194 described with respect to FIG. 7. At block 236, patient motion within the image data may be identified, similar to block 196 described with respect to FIG. 7.

At determination block 238, a physiological parameter within image data matching a physiological parameter within sensor data may be determined. For example, the computing system may compare a physiological parameter determined from the image data with a physiological parameter measured by the wearable device. For example, the patient may be attached to a wearable device that measures a respiratory rate. The computing system may be compared the measured respiratory rate and the respiratory rate determined based on the image data to adjust (e.g., increase, decrease) a confidence level in the measured physiological parameter.

If the physiological parameter within the image data matches the physiological parameter within the sensor data, then at block 239, the physiological parameter may be displayed on a graphical user interface. For example, the computing system may update a respiratory rate based on the sensor data, the image data, or both. To this end, the computing system may compare a physiological parameter determined from the image data with a physiological parameter measured by the wearable device. For example, the patient may be attached to a wearable device that measures a respiratory rate. The computing system may be compared the measured respiratory rate and the respiratory rate determined based on the image data to increase confidence in the measured physiological parameter. In other examples, the computing system may identify a patient motion, a patient posture, and the like within both the image data and the sensor data. Additionally or alternatively, the computing system may display the confidence level on the graphical user interface to indicate reliable data. The method 230 may return to block 232 to receive sensor data and image data.

If the patient motion within the image data does not match the patient motion within the sensor data, then at block 240, a time period with the unreliable data may be identified. The computing system may identify the time period in which the physiological parameter within the image data does not match the physiological parameter within the sensor data. In certain instances, the computing system may identify a time period in which the patient may be moving within the camera data and identify motion artifacts within the sensor data during the same time period.

At block 242, a previous physiological parameter may be held. For example, the computing system may not store the sensor data corresponding to the time period and instead hold a physiological parameter in the sensor data prior to the time period. That is, the computing system may store a physiological parameter with a high confidence level, thereby improving patient monitoring. Additionally or alternatively, the computing system may hold the previous physiological parameter on the graphical user interface for the clinician to view.

At block 244, a noise mitigation algorithm may be applied. The computing system may apply a noise mitigation algorithm to the sensor data over the period of time to remove motion artifacts (e.g., noise) from the sensor data. For example, the noise mitigation algorithm may be a bandpass filter, a high pass filter, a low pass filter, or any combination thereof. After applying the noise mitigation algorithm, the method 230 may return to determination block 238 to determine if the physiological parameter within the image data matches the physiological parameter within the filter sensor data. If the physiological parameters match, then the method 230 may continue to block 239 to display the physiological parameter on the graphical user interface. If the physiological parameters do not match, then the method 230 may continue to block 240 to identify the time period, and either hold the previous physiological parameter at block 242 or apply an additional noise mitigation algorithm at block 244. In this way, the physiological parameters displayed on the display device may be reliable, thereby improving patient care provided by the clinician.

The methods discussed herein include various steps represented by blocks in flow diagrams. It should be noted that at least some steps may be performed as an automated procedure by one or more components of a system. Although the flow diagrams may illustrate the steps in a certain sequence, it should be understood that the steps may be performed in any suitable order and certain steps may be carried out simultaneously, where appropriate. Additionally, steps may be added to or omitted from the methods.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

The invention claimed is:

1. A patient monitoring system comprising:

a camera acquiring image data in a field of view including a first patient and a second patient;

a first sensor coupled to the first patient and a second sensor coupled to the second patient; and a computing system communicatively coupled to the camera and the first sensor and the second sensor, the computing system performing operations comprising:

receive the image data from the camera;

identify the first patient in the image data based on biometric data of the first patient or a unique identifier of the first sensor;

identify the second patient in the image data based on biometric data of the second patient or a unique identifier of the second sensor;

receive, from the first sensor, first sensor data indicative of a first physiological parameter of the first patient;

receive, from the second sensor, second sensor data indicative of a second physiological parameter of the second patient;

display the image data;

overlay a first parameter set on the displayed image data at a first location proximate to the first patient, the first parameter set comprising the first physiological parameter;

overlay a second parameter set on the displayed image data at a second location proximate to the second patient, the second parameter set comprising the second physiological parameter;

dynamically change location of the first overlaid parameter set in the displayed image data based on movement of the first patient, such that the first overlaid parameter set tracks the movement of the first patient within the field of view; and dynamically change location of the second overlaid parameter set in the displayed image data based on movement of the second patient, such that the second overlaid parameter set tracks the movement of the second patient within the field of view.

2. The patient monitoring system of claim 1, wherein the computing system performs operations comprising:

associate the first sensor with the first patient based on the unique identifier of the first sensor and the second sensor with the second patient based on the unique identifier of the second sensor;

identify the unique identifier of the first sensor and the unique identifier of the second sensor within the image data; and associate the first parameter set with the identified first patient based on the unique identifier of the first sensor and the second parameter set with the second patient based on the second unique identifier of the second sensor.

3. The patient monitoring system of claim 1, wherein dynamically changing location of the first overlaid parameter set in the displayed image data comprises:

receiving updated image data from the camera;

identifying the first patient at an updated location in the updated image data;

displaying the updated image data; and moving the first overlaid parameter set on the displayed updated image data to be proximate the updated location of the first patient.

4. The patient monitoring system of claim 1, wherein the location of the overlaid first parameter set on the displayed image data is determined based on a location of the identified first patient in the image data, and wherein the location of the first parameter set of the identified first patient does not obscure or exclude a facial portion of the first patient.

5. The patient monitoring system of claim 1, wherein the computing system performs operations comprising:

identify a first value of the first physiological parameter of the first patient over a period of time based on the image data;

hold a second value of the first physiological parameter prior to the period of time based on the first sensor data in response to the first value of the first physiological parameter not matching a third value of the first physiological parameter of the first sensor data; and overlay or hold the second value of the overlaid first physiological parameter proximate to the identified first patient.

6. The patient monitoring system of claim 1, wherein the computing system performs operations comprising:

detect increased activity of the identified first patient over a period of time based on the image data; and apply a noise mitigation algorithm to the first sensor data during the period of time to hold the first physiological parameter during the period of time.

7. The patient monitoring system of claim 1, wherein the computing system performs operations comprising:

receive, from a third sensor coupled to a clinician in the field of view, a third parameter set indicative of a third physiological parameter of the clinician; and overlay the third parameter set at a location proximate the clinician in the image data.

8. The patient monitoring system of claim 1, wherein the computing system performs operations comprising:

display patient information associated with the identified first patient or the first sensor data in response to user selection of the identified first patient or a visual representation of the identified first patient in the image data.

9. The patient monitoring system of claim 1, wherein the first overlaid parameter set and the second overlaid parameter set are non-overlapping.

10. The patient monitoring system of claim 1, wherein the first sensor comprises a wearable device worn by the first patient and wherein the first overlaid parameter set is overlaid proximate the wearable device.

11. The patient monitoring system of claim 1, wherein the first patient is depicted in the displayed image data by a first avatar, and wherein the second patient is depicted in the displayed image data by a second avatar.

12. A patient monitoring system, comprising:

a camera acquiring image data in a field of view including a first patient and a second patient;

a first plurality of sensors coupled to a first patient in the field of view to generate first sensor data indicative of respective first physiological parameters of the first patient;

a second plurality of sensors coupled to a second patient in the field of view to generate second sensor data indicative of respective second physiological parameters of the second patient; and a computing system communicatively coupled to the camera and the first plurality of sensors and the second plurality of sensors, the computing system performing operations comprising:

receive the image data from the camera;

receive first patient biometric data and an association of the first plurality of sensors with the first patient biometric data;

receive second patient biometric data and an association of the second plurality of sensors with the second patient biometric data;

identify the first patient within the image data based on the first patient biometric data;

identify the second patient within the image data based on the second patient biometric data;

associate the first physiological parameters determined from the first sensor data with the identified first patient in the image data;

associate the second physiological parameters determined from second sensor data with the identified second patient in the image data;

display the image data;

display a first overlay at a first location in the displayed image data proximate to the first patient, the first overlay comprising the first physiological parameters, and display a second overlay at a second location in the displayed image data proximate to the second patient, the second overlay comprising the second physiological parameters; and anchor the first overlay to the first patient and the second overlay to the second patient such that the first overlay moves with the first patient within the displayed image data and the second overlay moves with the second patient within the displayed image data.

13. The patient monitoring system of claim 12, wherein the computing system performs operations comprising:

identify a patient activity of the first patient within the image data;

identify a corresponding activity of the first patient based on the first sensor data; and display a notification in response to the identified patient activity being different from the corresponding activity.

14. The patient monitoring system of claim 12, wherein the first overlay and the second overlay are visually separated from each other.

15. The patient monitoring system of claim 12, wherein partial overlay of the first overlay and the second overlay onto images of individuals not being monitored occurs when the image data is crowded.

16. A method of patient monitoring, comprising:

receiving, via a processor, image data in a field of view from a camera within a patient monitoring area;

identifying, via the processor, a first patient within the image data based on a unique identifier of a first-patient sensor attached to the first patient or biometric data of the first patient;

identifying, via the processor, a second patient within the image data based on a unique identifier of a second-patient sensor attached to the second patient or biometric data of the second patient;

receiving, via the processor, first-patient sensor data indicative of a physiological parameter of the first patient from the first-patient sensor and second-patient sensor data indicative of a physiological parameter of the second patient from the second-patient sensor;

creating, via the processor, a first-patient parameter set from the first-patient sensor data and a second-patient parameter set from the second-patient sensor data;

instructing, via the processor, a display device to display the image data and overlay the first-patient parameter set at a location proximate to the first patient and the second-patient parameter set at a location proximate to the second patient;

dynamically changing location of the overlaid first-patient parameter set in the displayed image data based on movement of the first patient, such that the overlaid first-patient parameter set tracks the movement of the first patient within the field of view; and dynamically changing location of the overlaid second-patient parameter set in the displayed image data based on movement of the second patient, such that the overlaid second-patient parameter set tracks the movement of the second patient within the field of view.

17. The method of claim 16, comprising:

determining, via the processor, a second physiological parameter of the first patient from the first-patient sensor using the image data; and outputting, via the processor, a notification of unreliable data in response to the second physiological parameter of the first patient from the first-patient sensor diverging from the first physiological parameter of the first patient from the first-patient sensor.

18. The method of claim 16, comprising:

determining, via the processor, patient activity of the first patient within the image data; and outputting, via the processor, a notification to check the first-patient sensor in response to the patient activity of the first patient within the image data being different from a patient activity of the first patient determined using the first-patient sensor data.

19. The method of claim 16, wherein the first-patient sensor data is graphically associated with the first patient or a visual representation of the first patient in the image data.

20. The method of claim 16, further comprising:

dynamically changing location of the overlaid first-patient parameter set to a location associated with a visual representation of a wearable device attached to the first patient and dynamically changing location of the overlaid second-patient parameter set to a location associated with a visual representation of a wearable device attached to the second patient.

* * * * *